United States Patent [19]
Skiba

[11] Patent Number: 5,480,447
[45] Date of Patent: Jan. 2, 1996

[54] JOINT IMPLANT

[75] Inventor: Jeffry B. Skiba, Tempe, Ariz.

[73] Assignee: International Polymer Engineering, Inc., Tempe, Ariz.

[21] Appl. No.: 310,928

[22] Filed: Sep. 22, 1994

Related U.S. Application Data

[63] Continuation of Ser. No. 990,415, Dec. 15, 1992, abandoned.

[51] Int. Cl.$^6$ ................................ A61F 2/30; A61F 2/42
[52] U.S. Cl. ................................................. 623/21; 623/18
[58] Field of Search ............................ 606/65, 66, 67; 623/21, 11, 18, 16

[56] References Cited

U.S. PATENT DOCUMENTS

| | | | |
|---|---|---|---|
| D. 277,509 | 2/1985 | Lawrence et al. | D24/33 |
| D. 277,784 | 2/1985 | Sgarlato et al. | D24/33 |
| D. 284,099 | 6/1986 | Laporta et al. | D24/33 |
| 3,990,116 | 11/1976 | Fixel et al. | 623/21 |
| 4,011,603 | 3/1977 | Steffee | 3/1.91 |
| 4,158,893 | 6/1979 | Swanson | 3/1.91 |
| 4,246,662 | 1/1981 | Pastrick | 3/1.91 |
| 4,313,232 | 2/1982 | Habal et al. | 3/1.91 |
| 4,634,445 | 1/1987 | Helal | 623/21 |
| 4,731,087 | 3/1988 | Sculco et al. | 623/21 |
| 4,863,444 | 9/1989 | Blomer | 606/67 |
| 4,969,909 | 11/1990 | Barouk | 623/21 |
| 5,062,851 | 11/1991 | Branemark | 623/18 |
| 5,098,779 | 3/1992 | Kranzler et al. | 428/306.6 |

FOREIGN PATENT DOCUMENTS 1266537  10/1986  U.S.S.R. ........................ 623/21

Primary Examiner—Debra S. Brittingham
Attorney, Agent, or Firm—David G. Rosenbaum

[57] ABSTRACT

A joint implant is presented having an elongated cylindrical member with an annular spacer which accommodates the diameter of the cylindrical member by fitting loosely over the cylindrical member. The ends of the elongated cylindrical member are designed for insertion into the intramedullary canals of adjacent bones while the annular spacer is designed to cushion the joint and maintain proper spacing between the bones.

10 Claims, 1 Drawing Sheet

JOINT IMPLANT

This is a continuation of application Ser. No. 07/990,415 filed on Dec. 15, 1992, now abandoned.

BACKGROUND OF THE INVENTION

The present invention relates generally to a joint prosthesis. More particularly, the present invention relates to a joint implant designed to replace the inter-phalangeal or metatarsal-phalangeal joints in the foot, or the inter-phalangeal or metacarpal-phalangeal joints in the hand. In addition, the joint implant may be scaled up to replace any linear joint between adjacent long bones.

Joint implants for replacing finger and toe joints are well known. For example, U.S. Pat. No. 4,246,662 describes a prosthetic joint comprising a one-piece body of flexible physiologically inert material having an enlarged central portion with two stem portions extending from opposite sides of the enlarged central portion. The enlarged central portion contains a slot which extends substantially through the central portion thereby forming a hinge for articulation of a joint. U.S. Pat. No. 4,313,232 discloses an elastomeric joint prosthesis for replacing damaged joints in humans. The joint prosthesis is substantially elongate with oppositely tapered ends and a wider central segment. The joint prosthesis is made of a biocompatible cloth mesh which is reinforced with an elastomer to provide lateral stability and enable the prosthesis to flex along a single plane. Bending occurs along a plane in the wider central segment of the blank. U.S. Pat. No. 4,634,445 describes a small joint spacing prosthesis having an elongate silicone rubber body which contains a Dacron or nylon string for reinforcement. The prosthesis further comprises a spherically shaped spacer in its middle having flat end faces for abutment with bone ends, and intramedullary stems extending from opposite sides of the spacer which are of lesser width than the spacer. The spacer and intramedullary stems comprise one continuous body. This patent also discloses that the bending of the joint prosthesis occurs in each of the stems and not in the spacer.

Therefore, there are no presently existing joint implants which form a structure comprising an elongated solid stem cylinder with a spacer which fits loosely over the cylinder thereby enabling the stem cylinder to flex during articulation of a joint at the point of the spacer, using the spacer as a fulcrum, but without substantial bending of the spacer.

SUMMARY OF THE INVENTION

Accordingly, it is a principal object of the present invention to provide a joint implant.

It is a further object of the present invention to provide an inter-phalangeal joint implant designed to replace the inter-phalangeal or metacarpal-phalangeal joints in the foot, or the inter-phalangeal or metacarpal-phalangeal joints in the hand.

It is a still further object of the present invention to provide a joint implant for the hands and feet which can be scaled up to provide a joint implant to replace any linear joint between long bones.

It is yet a further object of the present invention to provide a joint implant which comprises a structure and composition which, during the articulation of a joint, affords uniform flexibility along the length of the joint implant.

It is still a further object of the present invention to provide a joint implant which comprises a structure and composition which forestall the implant from loosening at those points where it is anchored into the intramedullary canals of adjacent bones.

In brief, there is provided a joint implant which includes an elongated solid cylinder and an annular spacer. The annulus of the spacer is of a size which accommodates the diameter of the elongated solid cylinder with a loose fit. The ends of the elongated cylinder are implanted into the intramedullary canals of adjacent bones so that the spacer resides intermediate along the length of the cylinder and separates the distal and proximal ends of the bones to which the joint implant is attached. Both the solid cylinder and the annular spacer are made of expanded polytetrafluoroethylene (PTFE), which is a highly biocompatible material.

These and other objects, features and advantages of the present invention will become more apparent to those skilled in the art from the following more detailed description of the preferred embodiment taken with reference to the accompanying drawings.

DETAILED DESCRIPTION OF THE PREFERRED EMBODIMENT

Figure 1:
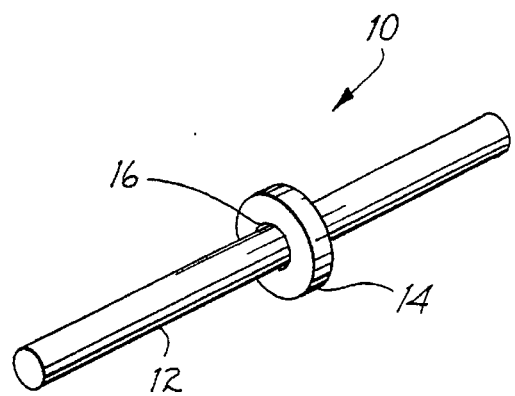
FIG. 1 is a perspective view of a joint implant in accordance with the present invention.

Turning now to the preferred embodiment of the present invention with reference to FIG. 1, the joint implant 10 of the present invention consists primarily of an elongated solid cylinder 12 and an annular spacer 14. The annulus 16 of the annular spacer 14 is of a size which accommodates the diameter of the elongated solid cylinder 12 with a loose fit.

When the joint implant 10 is properly seated to replace a joint, its configuration allows the elongated solid cylinder 12 to flex at the point of the annular spacer 14 during the articulation of the joint without substantially bending the annular spacer 14. The annular spacer 14 is used (acting as a fulcrum thereby enabling the elongated solid cylinder 12 to flex uniformly along its length) during joint articulation. The inventive joint implant 10 is advantageous over the joint implants described in the prior art in that the inventive joint implant 10 is able to impede the transference of stress resulting from joint articulation and thereby deter the joint implant 10 from loosening at those positions where it is anchored in the intramedullary canals of adjacent bones.

Both the elongated solid cylinder 12 and the annular spacer 14 are preferably made of expanded polytetrafluoroethylene (PTFE), which is a biocompatible thermoplastic polymer. Expanded PTFE comprises a porous microstructure of "nodes" and "fibrils". The fibers originate from the nodes with the nodes being generally thicker than the fibrils. The fibril length is controlled during processing and determines the porosity of the material.

PTFE is composed of long linear carbon chains surrounded by fluorine atoms. Expanded PTFE is hydrophobic as a result of the high electronegative charge of its polymer chains. Therefore, PTFE is less thrombogenic than other implant materials and virtually chemically inert.

Preferably, the joint implant is made of 100% PTFE, without additional copolymers, additives, or adhesives, thereby eliminating the possibility of leaching potentially bioreactive substances. Using 100% PTFE for the joint implant of the present invention is advantageous in that it provides a chemically inert and biocompatible implant which has a high tensile strength and a low coefficient of friction. The expanded PTFE which comprises the joint implant promotes tissue incorporation and revascularization, and implant anchoring. In addition, the pliability of the expanded PTFE provides the implant recipient with a comfortable fit.

Figure 2:
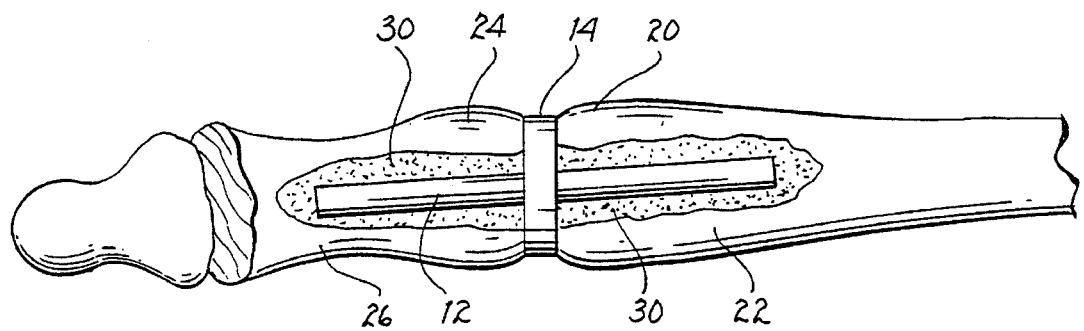
FIG. 2 is a side elevational view of a joint implant in accordance with the present invention shown implanted in posterior and anterior ends of proximal and middle phalangeal bones, respectively.

FIG. 2 illustrates the joint implant 10 shown implanted in the posterior end 20 of the proximal phalanx 22 and the anterior end 24 of the middle phalanx 26 in the foot of a recipient. Although reference is made here to the anatomical positioning of the implant at an inter-phalangeal joint in the foot, it should be understood by those skilled in the art that the inventive joint implant 10 is capable of replacing many other joints between bones, including the metatarsal-phalangeal joints in the foot, the inter-phalangeal or metacarpal-phalangeal joints in the hand, and other linear joints between long bones.

The surgical implant procedure can be performed on an outpatient basis using intravenous sedation and local anesthesia. First, a dorsilinear incision is made over the inter-phalangeal joint. Next, a linear incision is made through the extensor tendon apparatus and joint capsule thereby exposing the proximal inter-phalangeal joint. Both the posterior end 20 of the proximal phalanx 22 and the anterior end 24 of the middle phalanx 26 are dissected from any attachments and transversely osteomized with bone fragments being promptly excised.

The intramedullary canals 30 of both the proximal phalanx 22 and the middle phalanx 26 are then reamed with a 4.0 wire-pass drill to approximately one-half their length. After the reamed intramedullary canals 30 are flushed with an antibiotic solution, the elongated solid cylinder 12, which is flexible due to its expanded PTFE composition, is inserted into the reamed intramedullary canal 30 of the proximal phalanx 22.

Next, an appropriately sized annular spacer 14 is selected and placed over the elongated solid cylinder 12. The diameter of the annular spacer 14 should approximate the diameter of the proximal and middle phalanges 22, 26. That end of the elongated solid cylinder 16 which is exposed is then cut to fit the length of the reamed intramedullary canal 30 of the middle phalanx 26. The wound is closed following a visual check of the spacing and alignment of the joint.

Custom cutting the elongated solid cylinder 12 of the joint implant 10 at the time of surgery allows for the best fit in the reamed intramedullary canals, thereby providing flexibility in the joint while aligning the digits. The annular spacer 14 is designed to cushion the joint and maintain proper inter-digit spacing.

After implantation of the joint implant 10, tissue ingrowth will occur in the node and fibril structure of the expanded PTFE of the elongated solid cylinder 12 which is located in the intramedullary canals of the bones. However, although the annular spacer 14 is also composed of expanded PTFE, the excised ends of the adjacent bones which abut the annular spacer 14 will not exhibit tissue ingrowth to the extent realized in the elongated solid cylinder 12 in that the ends of the bones feature less tissue growth activity. This enables the annular spacer 14 to function as a fulcrum thereby allowing the stress resulting from joint articulation to be distributed uniformly along a flexible length of the elongated solid cylinder 16, as previously described.

Clinical Studies

Nineteen patients received a total of thirty-six joint implants in accordance with the present invention over a three month period. Patients were selected based on adequate vascular status, presence of fibro-osseous unions (joint fusions), progressive joint deformity, and intolerable pain with little or no peripheral inter-phalangeal joint (PIPJ) range of motion available. The structural joint changes of those patients selected no longer responded to conservative treatment. In addition, those patients with hammertoes often exhibited PIPJ subluxations/dislocations, often with various deformities.

The joint implant of the present invention was implanted in patients according to the surgical procedure previously described in the detailed description of the preferred embodiment of the invention. A result of the clinical trials showed patients with a significant digital re-alignment post-operatively, with a shorter post-operative recovery period and an earlier return to wearing normal footwear. The tests further demonstrated minimal to non-existent post-operative fibrositis, foreign body reaction, infection, and dislocation. Patients also exhibited limited to non-existent post-operative edema or pain. At twelve weeks, recipients of the inventive joint implants demonstrated a functional range of motion, stability, and good digital alignment.

While the preferred embodiment of the invention has been shown and described, it will be apparent to those skilled in the art that various changes and modifications may be made without departing from the true spirit and scope of the present invention. For that reason, the scope of the present invention is set forth in the following claims.

I claim:

1. A joint implant comprising:

a central stem having a longitudinal length and member forming both distal and proximal aspects of the joint implant when implanted into distal and proximal intramedullary canals of bone tissue surrounding a joint wherein said central stem member is substantially comprised of a deformabable microporous expanded polytetrafluoroethylene material having a node and fibril microstructure which allows tissue ingrowth into the node and fibril microstructure thereby anchoring the central stem member into the bone tissue to provide implant patency; and an annular spacer having an annulus which receives and accommodates the central stem member therethrough and acts as a fulcrum which allows the central stem member to flex along said longitudinal length at a position of the annular spacer without the annular spacer being substantially deformed whereby said central stem member is free to reciprocate in said annulus.

2. The joint implant according to claim 1, wherein said central stem member is uniformly flexible along a length of the central stem member.

3. The joint implant according to claim 2, wherein said annular spacer is compressible thereby enabling stress resulting from an articulation of a joint to be distributed along a full length of said central stem member.

4. The joint implant according to claim 3, wherein both said central stem member and said annular spacer are consisting essentially of expanded polytetrafluoroethylene.

5. A joint implant comprising:

an elongated cylinder having a longitudinal length and a uniform diameter throughout and first and second ends which are inserted into distal and proximal ends of adjacent bones, respectively, to which the joint implant is attached wherein each of said first and second ends of said elongated cylinder are susceptible to tissue ingrowth thereby anchoring said first and second ends into bone tissue in said distal and proximal ends of the adjacent bones to provide patency of the joint implant; and an annular spacer, having planar ends, which accommodates said uniform diameter by fitting loosely over said elongated cylinder such that when said joint implant is inserted into said adjacent bones, whereby said annular spacer acts as a fulcrum which allows the elongated cylinder to flex along said longitudinal length at a position of the annular spacer without the annular spacer being substantially deformed said annular spacer resides intermediate along a length of said elongated cylinder and said planar ends of said annular spacer abut said adjacent bones.

6. The joint implant according to claim 5, wherein said elongated cylinder is uniformly flexible along its length.

7. The joint implant according to claim 6, wherein said annular spacer is compressible thereby enabling stress resulting from an articulation of a joint to be distributed along a full length of said elongated cylinder.

8. The joint implant according to claim 7, wherein both said elongated cylinder and said annular spacer are consisting essentially of expanded polytetrafluoroethylene.

9. A joint implant comprising:

a solid elongated cylinder consisting essentially of microporous expanded polytetrafluoroethylene, said solid elongated cylinder having a longitudinal length and a uniform diameter throughout a longitudinal axis thereof and first and second ends which are inserted into distal and proximal ends of adjacent bones, thereby permitting tissue ingrowth into the microporous expanded polytetrafluoroethylene which fixedly anchors the first and second ends into the distal and proximal ends of the adjacent bones, respectively, to which the joint implant is attached; and an annular spacer consisting essentially of expanded polytetrafluoroethylene and having planar ends, wherein said annular spacer accommodates said uniform diameter of said solid elongated cylinder by slidably fitting over said solid elongated cylinder such that when said joint implant is inserted into said adjacent bones, whereby said annular spacer acts as a fulcrum which allows the elongated cylinder to flex along said longitudinal length at a position of the annular spacer without the annular spacer being substantially deformed, said annular spacer resides intermediate along a length of said solid elongated cylinder and said planar ends of said annular spacer abut said adjacent bones.

10. A method for implanting a joint implant between two adjacent bones comprising:

inserting a first end of a deformabable microporous central stem member having a longitudinal length and into an intramedullary canal of one of said two adjacent bones;

placing an appropriately sized annular spacer over said central stem member;

cutting a second end of said central stem member to fit a length of an intramedullary canal of another of said two adjacent bones such that said annular spacer resides intermediate along the length of said central stem member and acts as a fulcrum which allows the elongated cylinder to flex along said longitudinal length at a position of the annular spacer without the annular spacer being substantially deformed;

inserting said second end of said central stem member into said other of said two adjacent bones; and immobilizing the joint and two adjacent bones for a period of time sufficient to permit bone tissue ingrowth into the microporous structure of the first and second ends of the central stem member, after which the first and second ends of the central central stem member are anchored in and resident in the bone tissue during the patency of the joint implant.

* * * * *

UNITED STATES PATENT AND TRADEMARK OFFICE
CERTIFICATE OF CORRECTION

PATENT NO. : 5,480,447
DATED : January 2, 1996
INVENTOR(S) : Jeffry B. Skiba

It is certified that error appears in the above-indentified patent and that said Letters Patent is hereby corrected as shown below:

Column 2, line 39, after "used", delete "acting"--.

Signed and Sealed this

Ninth Day of April, 1996

Attest:

BRUCE LEHMAN

*Attesting Officer*  *Commissioner of Patents and Trademarks*